United States Patent
Baek (10) Patent No.: US 10,451,532 B2
(45) Date of Patent: Oct. 22, 2019

(54) PORTABLE VISCOMETER

(75) Inventor: Seong-Gi Baek, Pleasanton, CA (US)

(73) Assignee: RheoSense, Inc., San Ramon, CA (US)

( * ) Notice: Subject to any disclaimer, the term of this patent is extended or adjusted under 35 U.S.C. 154(b) by 593 days.

(21) Appl. No.: 13/094,710

(22) Filed: Apr. 26, 2011

(65) Prior Publication Data

US 2012/0096929 A1  Apr. 26, 2012

Related U.S. Application Data

(60) Provisional application No. 61/327,889, filed on Apr. 26, 2010.

(51) Int. Cl.
*G01N 11/08* (2006.01)

(52) U.S. Cl.
CPC ................... *G01N 11/08* (2013.01)

(58) Field of Classification Search
CPC ......... G01N 11/00; G01N 11/04; G01N 11/08
USPC ...................................... 73/54.13
See application file for complete search history.

(56) References Cited

U.S. PATENT DOCUMENTS

| | | | |
|---|---|---|---|
| 3,143,393 A * | 8/1964 | De Seguin Des Hons | 73/864.11 |
| 3,266,299 A | 8/1966 | Swank | |
| 3,683,678 A * | 8/1972 | Yau | G01N 30/00 73/64.54 |
| 3,990,295 A * | 11/1976 | Renovanz | G01N 33/487 73/54.09 |
| 4,122,708 A | 10/1978 | Maier | |
| 4,141,252 A * | 2/1979 | Lodge | G01L 19/0092 73/724 |
| 4,241,602 A | 12/1980 | Han et al. | |

(Continued)

FOREIGN PATENT DOCUMENTS

| | | |
|---|---|---|
| CA | 2131653 A1 | 3/1995 |
| CN | 1449491 A | 10/2003 |

(Continued)

OTHER PUBLICATIONS

PCT Application PCT/US2011/034002; filed Apr. 26, 2011; Seong-Gi Baek; International Search Report mailed Jan. 18, 2012.

(Continued)

*Primary Examiner* — Lisa M Caputo
*Assistant Examiner* — Alex Devito
(74) *Attorney, Agent, or Firm* — Morgan, Lewis & Bockius LLP (57) ABSTRACT

A portable viscometer includes a pump mechanism which cooperates with a positive displacement sample container referred to as a positive displacement pipette, for dispensing, at a known flow rate, a sample of liquid for which viscosity is desired to be determined. The dispensed liquid flows through a flow through miniature viscosity sensor having at least two pressure sensors which measure the pressure drop of the liquid as it flows through a rectangular flow channel, the pressure drop at the known flow rate being proportional to the viscosity. A controller controls operation of the viscometer and processes sensor data, and the resulting measurements of viscosity can be displayed on a display. The positive displacement pipette is removably positioned in the viscometer so that it can be removed from the viscometer when a viscosity test is completed and replaced with another positive displacement pipette containing another liquid to be tested.

28 Claims, 4 Drawing Sheets

(56) References Cited

U.S. PATENT DOCUMENTS

| | | |
|---|---|---|
| 4,284,604 A | 8/1981 | Tervamaki |
| 4,422,210 A | 12/1983 | Bergsand et al. |
| 4,574,622 A * | 3/1986 | Hatfield ................. 73/54.04 |
| 4,624,132 A | 11/1986 | Parnaby et al. |
| 4,793,174 A * | 12/1988 | Yau ........................ 73/54.04 |
| 4,874,500 A | 10/1989 | Madou et al. |
| 4,878,378 A | 11/1989 | Harada |
| 4,894,698 A | 1/1990 | Hijikigawa et al. |
| 4,916,678 A | 4/1990 | Johnson et al. |
| 4,920,787 A | 5/1990 | Dual et al. |
| 5,029,479 A | 7/1991 | Bryan |
| 5,058,435 A | 10/1991 | Terry et al. |
| 5,165,292 A | 11/1992 | Prohaska |
| 5,189,777 A | 3/1993 | Guckel et al. |
| 5,202,939 A | 4/1993 | Belleville et al. |
| 5,225,959 A | 7/1993 | Stearns |
| 5,304,487 A | 4/1994 | Wilding et al. |
| 5,317,870 A * | 6/1994 | Inagawa ............... B60T 8/4009 |
| | | 60/418 |
| 5,317,908 A | 6/1994 | Fitzgerald et al. |
| 5,347,851 A | 9/1994 | Grudzien, Jr. et al. |
| 5,392,117 A | 2/1995 | Belleville et al. |
| 5,485,753 A | 1/1996 | Burns et al. |
| 5,486,335 A | 1/1996 | Wilding et al. |
| 5,503,003 A | 4/1996 | Brookfield |
| 5,602,339 A | 2/1997 | Wareham |
| 5,663,503 A | 9/1997 | Dam et al. |
| 5,756,883 A | 5/1998 | Forbes |
| 5,770,160 A * | 6/1998 | Smith et al. ............. 73/864.13 |
| 5,983,727 A | 11/1999 | Wellman et al. |
| 6,010,461 A | 1/2000 | Haniff et al. |
| 6,032,689 A | 3/2000 | Tsai et al. |
| 6,062,088 A | 5/2000 | Ingrisch et al. |
| 6,078,706 A | 6/2000 | Nau et al. |
| 6,085,596 A | 7/2000 | Jensen et al. |
| 6,237,398 B1 | 5/2001 | Porat et al. |
| 6,240,770 B1 | 6/2001 | Raffer |
| 6,338,284 B1 | 1/2002 | Najafi et al. |
| 6,393,898 B1 | 5/2002 | Hajduk |
| 6,499,336 B1 | 12/2002 | Raffer |
| 6,575,019 B1 | 6/2003 | Larson |
| 6,681,616 B2 | 1/2004 | Spaid et al. |
| 6,725,725 B1 | 4/2004 | Werner et al. |
| 6,840,092 B2 | 1/2005 | Eggen et al. |
| 6,892,583 B2 | 5/2005 | Baek |
| 7,290,441 B2 | 11/2007 | Baek |
| 7,730,769 B1 | 6/2010 | Kwon et al. |
| 2002/0011095 A1 | 1/2002 | Park et al. |
| 2002/0148282 A1 | 10/2002 | Hajduk et al. |
| 2003/0079547 A1 | 5/2003 | Baek |
| 2003/0182991 A1* | 10/2003 | Spaid et al. .................. 73/54.04 |
| 2004/0037739 A1 | 2/2004 | McNeely et al. |
| 2004/0123649 A1 | 7/2004 | Spaid et al. |
| 2005/0005684 A1 | 1/2005 | Chien et al. |
| 2005/0183496 A1 | 8/2005 | Baek |
| 2005/0210964 A1 | 9/2005 | Baek |
| 2006/0003439 A1 | 1/2006 | Ismagilov et al. |
| 2006/0019407 A1 | 1/2006 | Fulton et al. |
| 2006/0070426 A1 | 4/2006 | Pelletier |
| 2006/0162438 A1 | 7/2006 | Schofield et al. |
| 2006/0263263 A1 | 11/2006 | Shimizu |
| 2008/0125700 A1* | 5/2008 | Moberg ............ A61M 5/14244 |
| | | 604/67 |
| 2008/0134765 A1 | 6/2008 | Baek |
| 2009/0004063 A1 | 1/2009 | Higashihara et al. |
| 2009/0216465 A1 | 8/2009 | Millet |
| 2010/0071442 A1 | 3/2010 | Moon, Jr. et al. |
| 2010/0240048 A1 | 9/2010 | Takagi |
| 2012/0075949 A1 | 3/2012 | Norcross, Jr. |
| 2012/0096929 A1 | 4/2012 | Baek |
| 2015/0168284 A1 | 6/2015 | Minton et al. |

FOREIGN PATENT DOCUMENTS

| | | |
|---|---|---|
| CN | 101124467 A | 2/2008 |
| DE | 19750131 A1 | 6/1999 |
| DE | 10215946 A1 | 11/2003 |
| EP | 0067605 | 12/1982 |
| JP | S56157839 A | 12/1981 |
| JP | S57-045430 | 3/1982 |
| JP | S5888637 A | 5/1983 |
| JP | S61-107251 | 5/1986 |
| JP | S61-190853 | 11/1986 |
| JP | S62-194441 | 8/1987 |
| JP | 6-201420 A | 7/1994 |
| JP | H07-502122 | 3/1995 |
| JP | H11-194084 | 7/1999 |
| JP | H11-248715 | 9/1999 |
| JP | 2006-322850 | 11/2006 |
| JP | 2007-528501 | 10/2007 |
| WO | WO-93/12410 A1 | 6/1993 |
| WO | WO 99/26048 A1 | 5/1999 |
| WO | WO 2003/038388 A1 | 5/2003 |
| WO | WO 2005/086883 | 9/2005 |
| WO | WO 2005/086883 A2 | 9/2005 |
| WO | WO 2009/104065 A1 | 8/2009 |
| WO | WO 2014/031639 A | 2/2014 |
| WO | WO 2015/157698 A1 | 10/2015 |

OTHER PUBLICATIONS

Baek, Notice of Allowance, U.S. Appl. No. 10/286,602, dated Sep. 29, 2004, 7 pgs.

Baek, Final Office Action, U.S. Appl. No. 11/132,093, dated Jan. 24, 2006, 10 pgs.

Baek, Office Action, U.S. Appl. No. 11/132,093, dated Aug. 8, 2005, 9 pgs.

Baek, Office Action, U.S. Appl. No. 11/078,015, dated Sep. 13, 2006, 8 pgs.

Baek, Final Office Action, U.S. Appl. No. 11/078,015, dated Mar. 27, 2007, 6 pgs.

Baek, Notice of Allowance, U.S. Appl. No. 11/078,015, dated Jul. 6, 2007, 4 pgs.

Baek, Notice of Allowance, U.S. Appl. No. 11/983,210, dated Apr. 12, 2010, 6 pgs.

Baek, Final Office Action, U.S. Appl. No. 11/983,210, dated Aug. 20, 2009, 9 pgs.

Baek, Office Action, U.S. Appl. No. 11/983,210, dated Dec. 16, 2008, 9 pgs.

Dziuban, J.A. et al., "Silicon Optical Pressure Sensor," Sensors and Actuators A (Physical), Apr. 1992, vol. A32, No. 1-3, pp. 628-631, Switzerland.

Chan M.A. et al., "A Micromachined Pressure Sensor with Fiber-Optic Interferometric Readout," Sensors and Actuators A (Physical), May 1994, vol. A43, No. 1-3, pp. 196-201, Switzerland.

Chien, R.D., et al., "Study on Rheological Behavior of Polymer Melt Flowing Through Micro-Channels Considering the Wall-Slip Effect," Journal of Micromechanics and Microengineering, May 15, 2005, pp. 1389-1396.

FISO Technologies, "Product Data Sheet, FOP-M In-Vivo Pressure Sensor," 2 pgs.

FISO Technologies, "Technical Note Series, Fiber-Optic Pressure Transducer," 4 pgs.

Lee, S.B. et al., "A Micromachined Interferometer for Dynamic High-Pressure Sensing (in automotive applications)," Sensors, Jun. 1996, vol. 13, No. 6, Helmers Publishing, USA, 1 pg.

Rheosense Inc., Communication Pursuant to Article 94(3) EPC, EP05728127.1, dated Jul. 12, 2013, 7 pgs.

Rheosense Inc., Communication Pursuant to Article 94(3) EPC, EP05728127.1, dated Mar. 13, 2009, 5 pgs.

Rheosense Inc., Communication Pursuant to Article 94(3) EPC, EP02802527.8, dated Nov. 6, 2013, 8 pgs.

Rheosense Inc., Communication Pursuant to Article 94(3) EPC. EP02802527.8, dated Jan. 18, 2011, 7 pgs.

Rheosense Inc., First Office Action, CN201180031161.1, dated May 6, 2014, 29 pgs.

(56) References Cited

OTHER PUBLICATIONS

Rheosense Inc., Second Office Action, CN201180031161.1, dated Jan. 9, 2015, 21 pgs.
Rheosense Inc., International Search Report and Written Opinion, PCTUS2008082669, dated Jun. 29, 2009, 7 pgps.
Rheosense Inc. (Baek), International Search Report and Written Opinion, PCTUS2005/007869, dated Sep. 21, 2006, 4 pgs.
Rheosense Inc., International Preliminary Report on Patentability, PCTUS2005/007869, dated Oct. 18, 2006, 4 pgs.
Rheosense Inc., International Search Report, PCTUS2002/35290, dated Mar. 24, 2003, 1 pg.
Rheosense Inc., International Preliminary Examination Report, PCTUS2002/35290, dated Nov. 8, 2004 3 pgs.
Rheosense Inc., Notification to Grant Patent, CN200580014842.1, dated Dec. 2, 2010, 2 pgs.
Rheosense Inc., Second Office Action, CN200580014842.1, dated Jul. 12, 2010, 6 pgs.
Rheosense Inc., First Office Action, CN200580014842.1, dated Jan. 16, 2009, 13 pgs.
Rheosense Inc., Certificate of Patent, JP2007-502978, dated Sep. 16, 2011, 3 pgs.
Rheosense Inc., Notification of Reasons for Rejection, JP2007-502978, dated Nov. 9, 2010, 2 pgs.
Rheosense Inc., Notification to Grant Patent, CN02826519.X, dated Dec. 28, 2007, 2 pgs.
Rheosense Inc., First Office Action, CN02826519.X, dated Oct. 21, 2005, 10 pgs.
Rheosense Inc., Certificate of Patent, JP2003-540610, dated Mar. 6, 2009, 2 pgs.
Rheosense Inc., Notification of Reason for Rejection, JP2003-540610, dated Jul. 29, 2008, 2 pgs.
Rheosense Inc., Certificate of Patent, JP2008-159808, dated Jul. 8, 2011, 3 pgs.
Rheosense Inc., Notification of Reason for Rejection, JP2008-159808, dated Dec. 14, 2010, 1 pg.
Rheosense Inc., Letters Patent, KR10-2004-7006615, dated Apr. 26, 2010, 2 pgs.
Rheosense Inc., KIPO's Notice of Preliminary Rejection, KR10-2004-7006615, dated Sep. 11, 2009, 7 pgs.
Rodd, et al., "The Inertio-Elastic Planar Entry Flow of Low Viscosity Elastic Fluids in Micro-Fabricated Geometries," Journal of Non-Newtonian Fluid Mechanics 129, Jan. 2005, pp. 1-22.
Wagner, C., et al., "Optical Pressure Sensor Based on a Mach-Zehnder Inteferometer Integrated with a Lateral a-Si: H p-i-n Photodiode," IEEE Photonics Technology Letters, Oct. 1993, vol. 5, No. 10, pp. 1257-1259, USA.
Rheosense Inc., Third Office Action, CN201180031161.1, dated Jul. 13, 2015, 3 pgs.
Rheosense Inc., International Search Report and Written Opinion, PCTUS2015/025417, dated Jul. 24, 2015, 20 pgs.
Rheosense Inc., International Preliminary Report on Patentability, PCTUS2015/025417, dated Oct. 12, 2016, 18 pgs.
Rheosense Inc., Certificate of Patent, JP2013-508172, dated Nov. 18, 2016, 3 pgs.
Rheosense Inc., Intention to Grant, EP02802527.8, dated Jul. 5, 2017, 5 pgs.
Rheosense Inc., Extended European Search Report, EP11777928.0, dated Oct. 18, 2017, 11 pgs.
Rheosense Inc., Communication Pursuant to Rules 70(2) and 70a(2), EP11777928.0, dated Nov. 7, 2017, 1 pg.
Baek, Notice of Allowance, U.S. Appl. No. 15/290,936, dated May 14, 2019, 9 pgs.
Baek, Office Action, U.S. Appl. No. 15/290,936, dated Nov. 8, 2018, 20 pgs.
Rheosense Inc., 1st Office Action, CN201610164123.8, dated Dec. 26, 2017, 17 pgs.
Rheosense Inc., 2nd Office Action, CN201610164123.8, dated Nov. 15, 2018, 13 pgs.
Rheosense Inc., Communication Pursuant to Rules 161(2) and 162, EP15777447.2, dated Mar. 20, 2017, 2 pgs.
Rheosense Inc., CN201580030961, Office Action, dated Aug. 31, 2018, 22 pgs.
Rheosense Inc., Notification of Reason for Rejection, JP2017-504623, dated Dec. 26, 2017, 11 pgs.
Rheosense Inc., Notification of Reason for Rejection, JP2017-504623, dated Dec. 4, 2018, 17 pgs.
Rheosense, Inc. International Preliminary Report on Patentability, PCT/US2017/056097, dated Apr. 16, 2019, 10 pgs.
Rheosense, Inc. International Search Report/Written Opinion, PCT/US2017/056097, dated Dec. 18, 2017, 12 pgs.
Rheosense, Inc., Second Office Action, CN App. No. 20580030961, dated Jul. 18, 2019, 9 pgs.
Rheosense, Inc., Communication pursuant to Article 94(3), EP App. No. 15777447.2, dated Aug. 12, 2019, 13 pgs.
Rheosense, Inc., Third Office Action, CN Patent Application No. 201610164123.8, dated Mar. 21, 2019, 15 pgs.
Rheosense, Inc., Notification to Grant Patent Right for Invention, CN Application No. 201610164123.8, dated Aug. 12, 2019, 6 pgs.

* cited by examiner

Figure 5

PORTABLE VISCOMETER

PRIORITY CLAIM

This application claims the benefit of provisional application Ser. No. 61/327,889, filed Apr. 26, 2010, entitled "Portable Rheometer," which is incorporated herein by reference.

BACKGROUND

Field of the Invention

This invention is in the field of viscometers that measure viscosity of liquids utilizing a flow-through type viscosity sensor.

State of the Art

Viscosity is a measure of resistance of liquid to flow and its value depends on the rate of deformation for Non-Newtonian liquids as described in Dynamics of Polymeric Liquids, Vol. 1, 1987, authored by R. B. Bird, R. C. Armstrong, and O. Hassager. The rate of deformation is given by a shear rate in a unit of $(\text{time})^{-1}$. The viscosity measured at a known shear rate is "true" viscosity. The dependence of the true viscosity on shear rate is a viscosity curve which characterizes material and is an important factor to consider for efficient processing. However, in many cases, viscosity is measured under ill-defined test condition so that shear rate cannot be known or calculated. Under ill-defined conditions, the measured viscosity value is only "apparent". Since the true viscosity is measured at a known shear rate, the true viscosity is universal whereas the apparent viscosity is not. Instead, the apparent viscosity depends on the measuring system. For example, as a common practice, a torque of a spindle immersed in a sea of test liquid is measured while the spindle is being rotated at a constant speed. In this case the torque value only yields an apparent viscosity since the test condition is ill-defined and a shear rate is not known. At best, the apparent viscosity can be measured as a function of the rotational speed of the spindle. The rotational speed of the spindle can be in fact correlated with the shear rate only if a "constitutive equation" for the test liquid is known. However, a "constitutive equation" is not known for almost all Non-Newtonian liquids. Therefore, true viscosity can not be measured with ill-defined test conditions for most non-Newtonian liquids.

Methods of viscosity measurement that give only apparent viscosities have been developed and used for quality controls in manufacturing and material characterization. Various on-line viscometers are designed for real time viscosity measurement. U.S. Pat. No. 5,317,908 (Fitzgerald et al.) and U.S. Pat. No. 4,878,378 (Harada) are concerned with systems that measure apparent viscosities for process controls. U.S. Pat. No. 6,393,898 (Hajduk et al.) describes a system that measures many test liquids simultaneously. These viscometers measure apparent viscosities. However, because of the non-universality of the apparent viscosity measurement, a correlation of the apparent viscosity of a specific sample measured with a specific method with the true viscosity has to be found separately when desired. Fundamental development of formulations for materials requires the true viscosity measurement. Also the designs of processing equipments and accessories, such as dies, molds, extrusion screws, etc., require the true viscosity of the materials. However, the apparent viscosity measurement has been used for a quick test as an indication since it is easier and faster to measure and often more economical. The true viscosity is more difficult to get and can be only measured with a few types of instruments: rheometers and capillary viscometers. The rheometers impose a precise and known shear rate on test samples, thereby measuring true viscosities. The rheometers are versatile and usually equipped to also measure other properties. Therefore they are usually expensive. Further, large amounts of samples are usually required for viscosity measurement with a rheometer. Also, rheometers are not well suited for on-line applications. Circular capillary viscometers can measure apparent and true viscosities depending on whether a proper compensation is taken into account. The capillary viscometer needs a pressure drop measurement along the capillary for viscosity. Since the capillary is circular in cross-section, only pressure at the entrance and exit can be measured. Because of this limitation, the capillary viscometer measures only apparent viscosity unless the entrance effect is corrected for by using two different capillaries with different length to diameter ratios. However, use of two capillaries makes the capillary viscometers bulky and/or time consuming. Capillary viscometers are described in U.S. Pat. No. 6,575,019 (Larson); U.S. Pat. No. 4,920,787 (Dual et al.); U.S. Pat. No. 4,916,678 (Johnson et al.); and U.S. Pat. No. 4,793,174 (Yau). Microfluidic viscometers are disclosed in U.S. Pat. No. 6,681,616 (Michael Spaid et al.) and Publication No. 2003/0182991 (Michael Spaid et al.). Residence time of a marker in a fluidic channel is used to measure the viscosity, which is not a true viscosity unless the test liquid is Newtonian. Only an apparent viscosity is measured for non-Newtonian liquids. The portable viscometer disclosed in U.S. Pat. No. 5,503,003 (Brookfield) utilizes a well known torque measurement of a spindle rotating in a sea of liquid for viscosity measurement. As indicated, and as is well known, this method only measures apparent viscosity.

In summary, most viscosity measurement techniques yield apparent viscosity and require relatively large volumes of sample. Also, these instruments require cleaning of the parts in contact with liquid (container, spindle, etc.) before the measurement of the next sample. Such a cleaning is time consuming so that viscosity measurements typically take about 30 minutes from the set-up to the test. The larger sample volume requirement with current techniques also increases the cleaning time and waste. Therefore, there is no genuine portable viscometer which measures true viscosity for samples in small quantity and in a fast manner. The slit viscometer disclosed in my U.S. Pat. No. 7,290,441 makes it possible to measure the true viscosity of small samples. It requires, however, a precision liquid dispensing system and associated electronics to provide and control the flow of liquid through the viscometer. A simple precision liquid dispensing system which is portable and can be use with a variety of samples is not disclosed in the prior art.

SUMMARY OF THE INVENTION

According to the current invention, a portable viscosity measurement instrument or viscometer includes a miniature viscosity measurement sensor, a portable precision liquid dispensing system for forcing a liquid sample through the miniature viscosity measurement sensor, a controller for controlling operation of the viscometer, and a display for displaying the measured viscosity of the liquid. The sensor design is described in my U.S. Pat. Nos. 6,892,583 and 7,290,441, which are hereby incorporated by reference as if fully set forth herein. The portable system of the current invention measures the true viscosity of a liquid and requires only small volume samples of the liquid for measurement. The invention also provides a fast and easy way to obtain samples of liquid to be tested and to insert the samples of liquid into the viscometer for testing.

The portable precision liquid dispensing system of the invention includes a positive displacement pump which operates in conjunction with a positive displacement sample container, which will be referred to as a positive displacement pipette, in which the sample of the liquid for which the viscosity is to be measured is supplied. The pipette may be removable from and replaceable in the viscometer so that a sample of liquid to be tested can be drawn into the pipette when removed and separate from the viscometer and the pipette with the sample of liquid therein then inserted into the viscometer for measuring the viscosity of the sample of liquid in the pipette. The pipette includes a plunger that slides within the pipette to draw a sample into the pipette (this can be done by hand) and to force the sample from the pipette when in the viscometer. In one embodiment of the positive displacement pump, a precision motor drives a lead screw which moves a push back in contact with the pipette plunger when positioned in the viscometer. As the push back moves the plunger in the pipette, liquid is dispensed from the pipette into a flow passage of the miniature viscosity measurement sensor. Control electronics control operation of the precision motor to dispense the liquid to be tested from the pipette at a known flow rate into the flow passage of the miniature viscosity measurement sensor.

The miniature flow-through viscosity measurement sensor includes a micron scale flow channel combined with a pressure sensor array which measures the pressure drop of a fully developed flow of the liquid in the flow channel. The pressure drop is proportional to the shear stress of the liquid flowing through the channel. The shear rate is proportional to flow rate. Viscosity of the sample liquid is calculated by dividing the shear stress by the shear rate. The resulting measurement of viscosity can be shown in a display. Microcontroller or microprocessor based electronics can form the controller electronics of the viscometer to control the motor of the pump and process the data from the pressure sensors. The processed data can be displayed and may also be stored and/or sent to remote devices.

If temperature control of the sample is desired, the viscometer, the viscosity sensor, and/or the sample in the pipette may be conditioned to a set temperature with a peltier based temperature control device or other generally accepted temperature control means.

The viscometer may store a history of measured viscosity values for various uses and/or may store a database of the known viscosity values of various liquids, such as liquids frequently expected to be measured. This can allow a quick comparison of the known viscosity of a known liquid with the measured viscosity of a sample thought to be the known liquid. Discrepancies between the known value and the measured value can indicate that the test liquid is not the liquid it is thought to be or can indicate problems with the viscometer so that the viscometer can be checked.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Reference will now be made to the exemplary embodiments illustrated, and specific language will be used herein to describe the same. It will nevertheless be understood that no limitation of the scope of the invention is thereby intended

DETAILED DESCRIPTION OF EXAMPLE EMBODIMENT(S)

Figure 1:
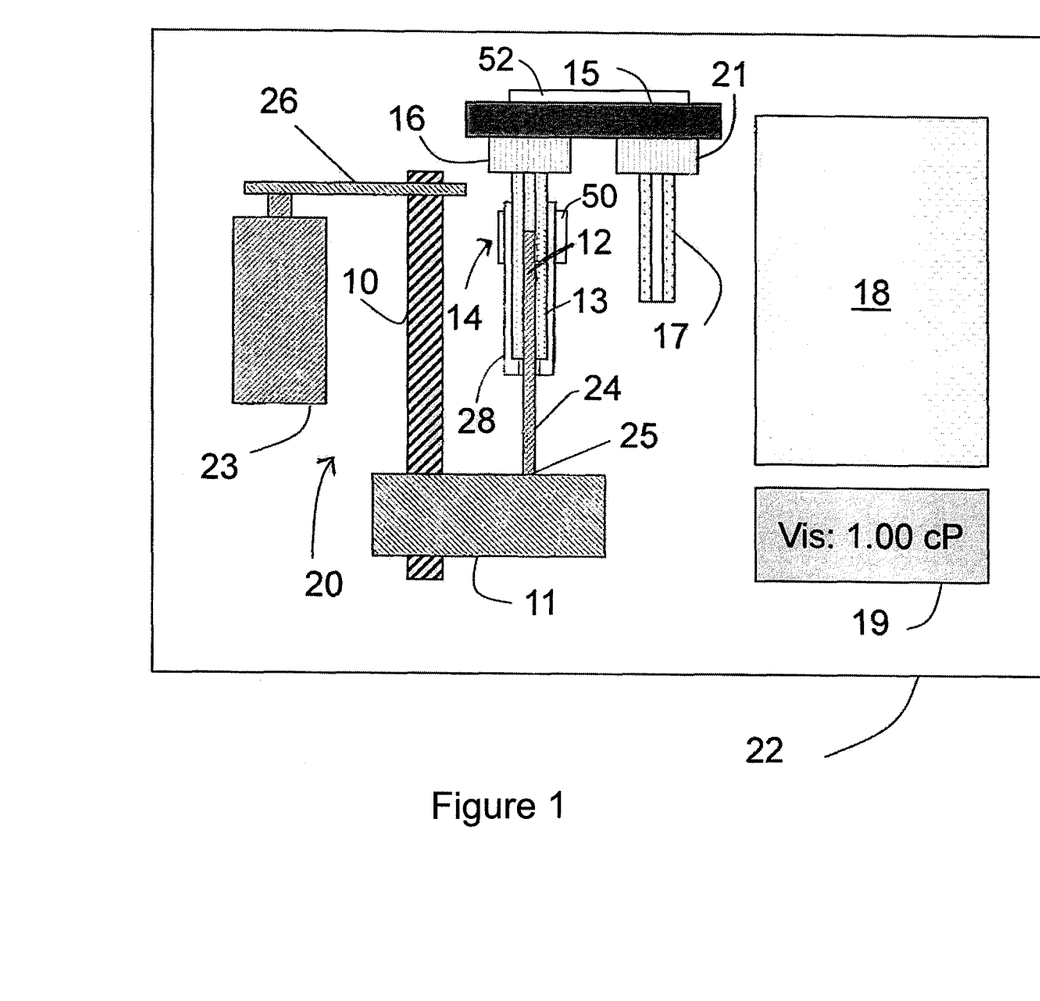
FIG. 1 is a schematic representation of a portable viscometer of the invention.

The invention provides an improved viscometer which is portable, easier-to-use, more accurate, and a faster way of measuring the viscosities of liquid samples than prior art viscometers. Referring to FIG. 1, the viscometer 22 includes a precision pump, indicated generally by reference number 20, a liquid container 14 for supplying a sample of the liquid for which a viscosity measurement is desired, a flow-through viscosity sensor 15, a controller 18, and a display 19.

The pump 20 works in conjunction with a sample container shown and referred to as a pipette 14 having a pipette barrel or body 13 and a plunger 12 slidably positioned in the pipette barrel 13 with plunger end portion 24 extending from an end of the barrel 13. The pipette 14 may be removably positioned and held in the viscometer by a mounting mechanism 28 so the pipette can be removed, filled with a sample of liquid to be tested, and replaced into the mounting mechanism of the viscometer, or can be removed and replaced with another similar pipette containing a sample of liquid to be tested. The pipette may be made disposable so a new, clean pipette is used for each sample of liquid. The pump includes a precision motor 23, a lead screw 10 rotatable by the motor 23 through a drive mechanism 26, such as a gear drive or belt drive, and a push back 11 mounted on lead screw 10 which contacts the end 25 of pipette plunger end portion 24 when pipette 14 is positioned in the viscometer. The push back 11 moves laterally along lead screw 10 in response to the rotation of the lead screw 10 by motor 23.

Figure 3:
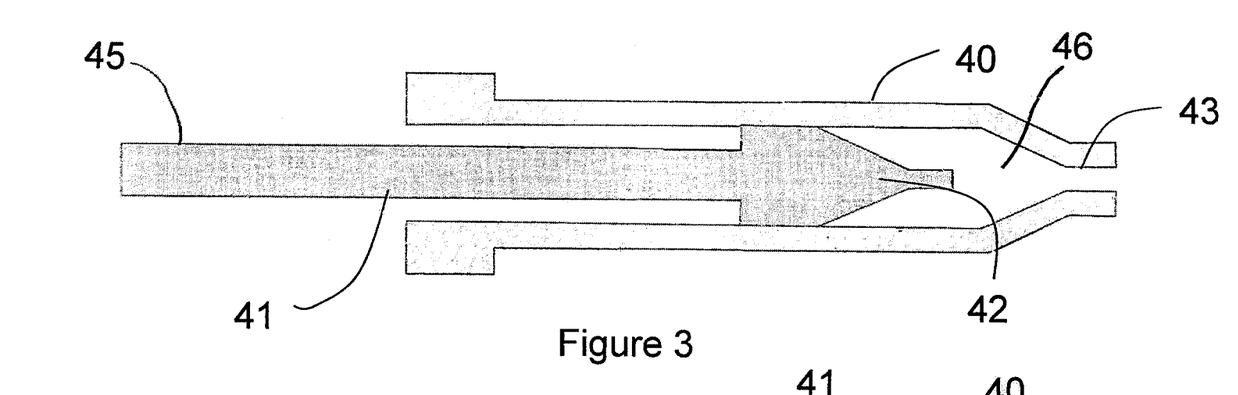
FIG. 3, a cross-sectional view of a pipette useable in the system of the invention showing the pipette plunger in an intermediate position in the pipette.
Figure 4:
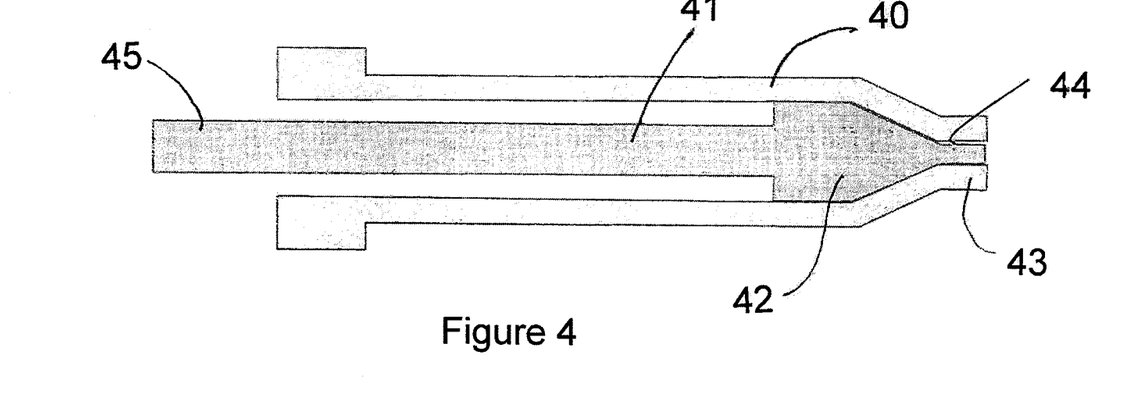
FIG. 4, a similar cross-sectional view of the pipette of FIG. 3 showing the pipette plunger in position before a sample of liquid has been drawn into the pipette or after the sample of liquid has been dispensed from the pipette, and FIG. 5, a schematic representation of a portable viscometer of the invention as shown in FIG. 1 including additional temperature conditioning devices.

An example of a pipette construction usable with the invention is shown in FIGS. 3 and 4. A pipette plunger 41 has a plunger head 42 sealingly and slidably received in pipette barrel 40 with an end portion 45 extending from an end of the pipette barrel 40. Both the pipette barrel and pipette plunger can be fabricated from plastic by injection molding. The plunger can slide back and forth inside of the barrel 40. In order to minimize air entrapment when filling the pipette with sample liquid, the end of plunger head 42 is shaped to closely fit into liquid flow barrel end 43, as shown in FIG. 4, to minimize any air gap 44 between the two. With the pipette in the condition shown in FIG. 4, the liquid flow end 43 of the pipette can be inserted into a liquid for which the viscosity is to be determined. A user can grasp the end portion 45 of the plunger 41 extending from the pipette barrel 40 and pull the plunger back from the end 43 of the pipette barrel to draw sample into the pipette barrel through an opening in barrel end 43. FIG. 3 shows the plunger 41 pulled back from the barrel end to create space 46 in the pipette barrel which will contain the liquid sample drawn into the pipette. As the pipette plunger 41 continues to be pulled back in pipette barrel 40, sample will continue to be drawn into the increasing space 46. The user stops pulling back the plunger 41 when the desired amount of sample is drawn into the pipette barrel. If the plunger 41 is pushed toward the liquid flow end 43 of the barrel 40, fluid in space 46 is discharged from the barrel 40 though the opening in barrel end 43.

Flow-through viscosity sensor 15 includes a liquid inlet connector 16 and a liquid outlet connector 21. As shown in FIG. 1, the liquid discharged from the end of the pipette barrel 13 is coupled through liquid inlet connector 16 to a liquid entrance to the viscosity sensor 15. A liquid discharge tube 17 is coupled through the liquid outlet connector 21 to guide liquid away from a liquid exit of viscosity sensor 15.

Figure 2:
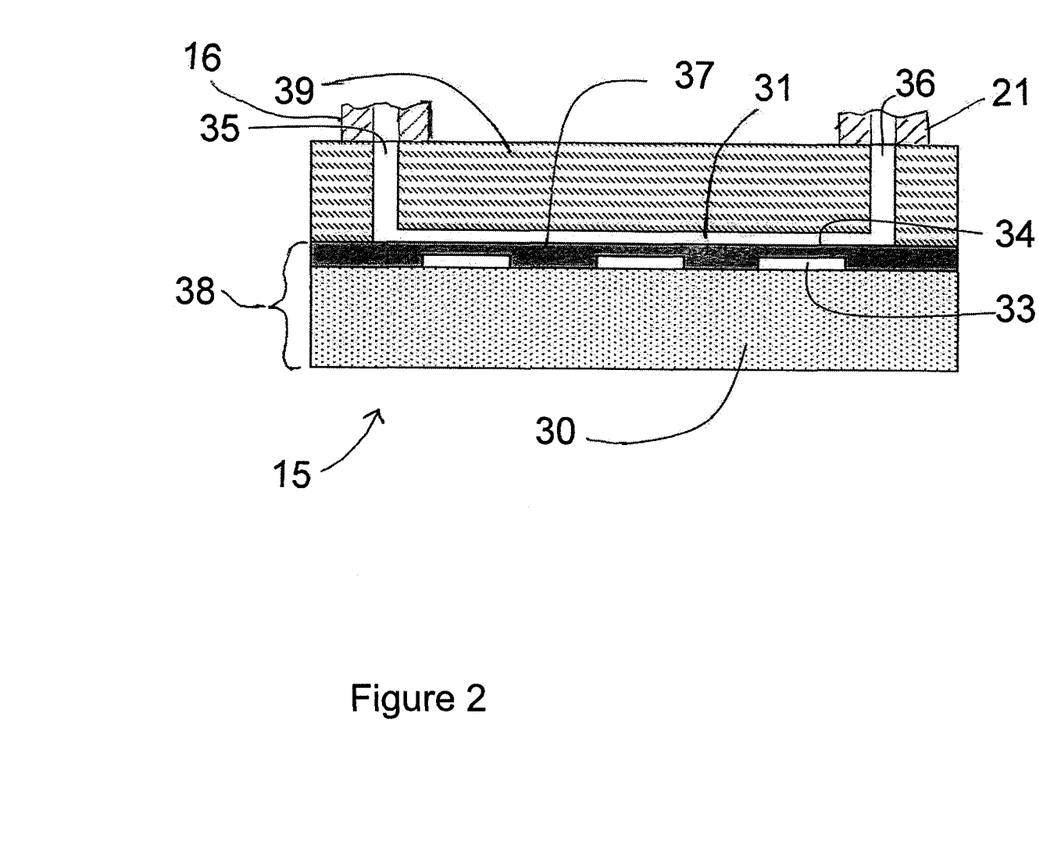
FIG. 2, a schematic cross-sectional representation of a flow-through viscosity sensor of the invention.

Referring to FIG. 2, the flow-through viscosity sensor 15 includes a liquid flow channel 31, with a flow channel entrance 35 and flow channel exit 36 formed in a channel substrate 39. The flow channel 31 has a rectangular cross-section with the channel substrate 39 providing three sides of flow channel 31, leaving one open side. A monolithic sensor plate 38 formed by a pressure sensor membrane 37 and a pressure sensor substrate 30 is combined with the channel substrate 39 to close the open side of flow channel 31. Monolithic sensor plate 38 provides a plurality of independent pressure sensors and is positioned with respect to the channel substrate 39 to locate at least two independent pressure sensors along the flow channel 31 spaced sufficiently away from the channel entrance 35 and channel exit 36 whereby a pressure drop of fully developed flow of liquid through the flow channel 31 can be measured by the pressure sensors. In the embodiment shown in FIG. 2, three independent pressure sensors are provided by the monolithic sensor plate 38 along flow channel 31. Each of the independent pressure sensors is formed by a cavity 33 in the pressure sensor membrane 37. The portions 34 of the pressure sensor membrane 37 that extend over the respective cavities 33 will deflect into the respective cavities 33 upon application of pressure to such portions 34 of the pressure sensor membrane extending over the respective cavities 33. The amount of deflection into a respective cavity is proportional to the pressure applied by the liquid flowing in the flow channel 31 to the pressure sensor membrane over the respective cavities.

A detector is provided in each of the cavities for detecting the displacement of the membrane into the respective cavity which provides a measurement of the pressure applied to the membrane over the cavity. Various detectors can be used, such as a capacitance detector wherein one capacitor electrode is located on the pressure sensor membrane over a cavity and the other capacitor electrode is located on the sensor substrate 30 covering the cavity. Displacement of the membrane moves the capacitor electrodes closer together and changes the capacitance which provides the measure of pressure. It will be noted that the surface of the pressure sensor membrane 37 along the liquid channel 31 is substantially a smooth continuous surface without individual pressure sensors being inserted into the surface to form irregularities and discontinuities. This smooth channel surface is important to obtaining accurate pressure measurements. A more detailed description of the pressure sensor and variations and different embodiments of the flow-through viscosity sensor construction are provided in my U.S. Pat. Nos. 6,892,583 and 7,290,441, hereby incorporated by reference into this disclosure. Liquid inlet connector 16 attached to channel substrate 39 around liquid channel entrance 35 provides for connection of a source of pressurized sample liquid, here liquid discharged from pipette 14, and liquid outlet connector 21 attached to channel substrate 39 around liquid channel exit 36 provides for connection to a sample liquid drain or holding reservoir.

Controller 18 includes one or more microcontrollers or microprocessors, and other electrical and electronic components for controlling operation of the viscometer and peripheral components, for performing calculations, for controlling the display 19 which can display the measured viscosity and other information such as status of the viscometer, and for communicating with and transferring data to other equipment such as other computers. Communication can be through ports such as RS232 or USB ports or can be through wireless or other communication means. Controller 18 will generally include interface means, such as a keyboard, touch button pad or key pad, an external computer, or other data entry means such as buttons, a mouse, or a touch screen in display 19, whereby a user can enter control and other instruction and information into the controller.

To measure the viscosity of a sample of liquid, a sample of the liquid for which the viscosity is to be determined is obtained in a liquid sample holding pipette. The sample of liquid in the pipette can have been withdrawn from a source of the liquid into the pipette by the user of the viscometer or can be otherwise supplied to the user of the viscometer in the pipette. As shown in FIG. 1, the pipette 14 is mounted in the viscometer 22 and is held in position in the viscometer by mounting mechanism 28. The controller is then activated to control the viscometer to make a viscosity measurement. The controller will operate the motor 23 to advance the push back 11 to a position as shown in FIG. 1 against the end 25 of the pipette plunger. Alternatively, the push back 11 could be positioned, such as manually, by the user when the pipette is mounted in the viscometer prior to activation of the controller.

With the push back 11 in position against the end 25 of the pipette plunger, the controller controls the motor 23 so as to rotate lead screw 10 to advance the push back 11 and pipette plunger 12 at a desired speed or speeds to discharge the liquid from the pipette at a known desired flow rate or flow rates. As the plunger moves, the liquid is forced from the pipette into the viscosity sensor 15 and flows through the flow channel 31 in which the pressure drop of a fully developed flow of the liquid is measured by the pressure sensors of the monolithic pressure sensor 38. The pressures are measured as the local pressures over respective membrane portions of the pressure sensors along the flow channel 31 deflect sensor membrane portions 34 into respective cavities 33. The pressure drop measured along the flow channel 31 (the difference in pressures measured between successive pressure sensors along the flow channel) is proportional to the viscosity of the liquid at the specific flow rate. If the sample viscosity varies with the flow rate, then the control can be instructed to dispense the liquid at different flow rates in sequence, with or without flow stoppage. When the pressure values are acquired and the viscosity values calculated as a function of flow rate, the relationship is corrected for non-Newtonian viscosity in a known manner. The measured viscosities may be displayed on the display 19, may be stored in a controller memory or auxiliary memory, and/or transmitted to a remote memory or computer.

As the liquid is injected into liquid flow channel 31 in the viscosity sensor 15 at an initially set flow rate (or shear rate), the viscometer senses the pressure inside the liquid flow channel 31. The controller can be programmed to determine if the pressure level is optimal for the highest accuracy or assured accuracy of the viscosity measurement. If the pressure level is too low, the controller determines and sets the next flow rate value and ramps up the flow rate to the new set value. The controller continues the iteration to reach the optimal flow rate for the particular viscosity measurement. In this way, viscosity of unknown liquids can be accurately and automatically measured.

When the viscosity measurement or measurements for a sample of liquid have been obtained, the push back 11 is operated to move it back to a position to allow the used pipette to be removed and a new pipette with a sample of new liquid therein for testing to be inserted in the viscometer. The pipette with the sample of new liquid to be tested may be a new disposable pipette or a reloaded used pipette. For the new viscosity measurement, the controller operates the viscometer as described above to determine the viscosity of the sample of new liquid. In this test, the liquid from the new sample displaces the liquid from the old sample in the viscosity sensor 15. In this way, no cleaning of the viscosity sensor is needed. If the two successive liquids to be tested are not compatible or miscible, then the viscosity sensor 15 needs to be cleaned with a cleaning liquid compatible to both liquids to be tested prior to dispensing the new liquid into the viscosity sensor 15. This cleaning can be done by loading a pipette containing the cleaning liquid into the viscometer and operating the viscometer to force the cleaning liquid through the viscosity sensor 15 between the two liquids being tested.

The viscometer 22 may be powered by a battery, such as a rechargeable battery, so that it is truly portable, or may be powered by connecting it to a source of power as it is moved from place to place.

Figure 5:
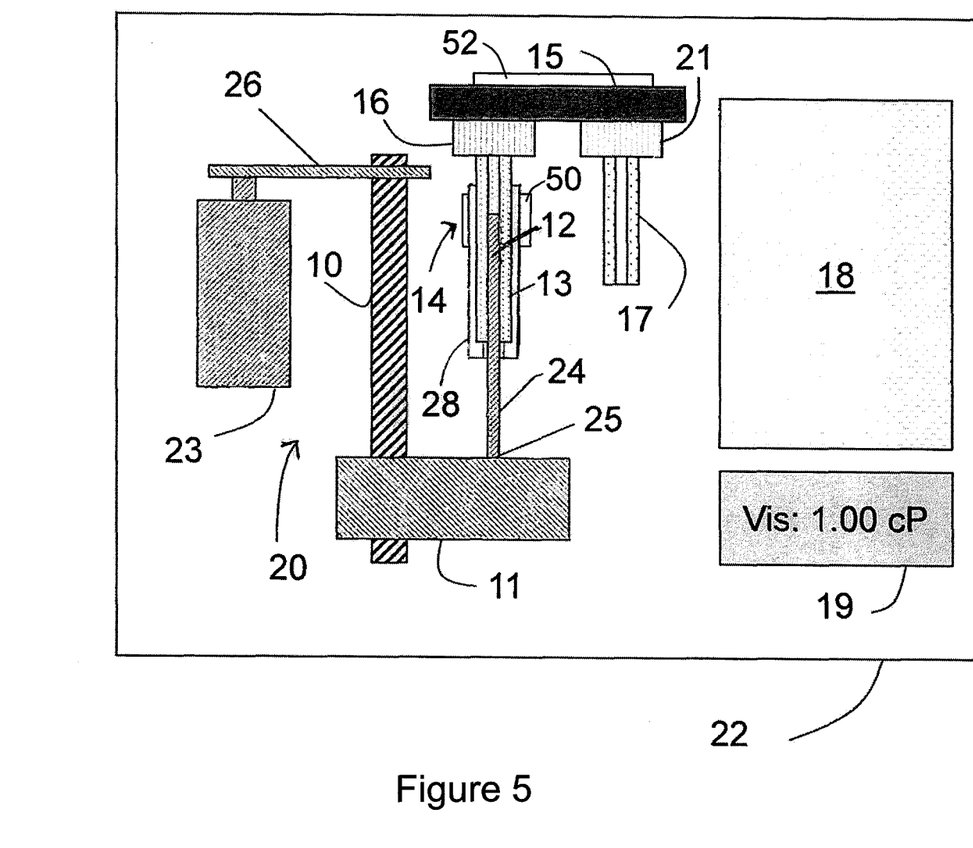

In some instances it may be desirable to control the temperature of the liquid for which the viscosity is being measured. If temperature control is desired, the viscometer 22, the viscosity sensor 15, and/or the sample in the pipette 14 may be conditioned at a set temperature with a peltier based temperature control device or other generally accepted temperature control means. For example, as shown in FIG. 5, which is similar to FIG. 1, a temperature control device 50 may be placed in or in contact with pipette mounting mechanism 28 so as to heat or cool a liquid sample holding pipette 14 and the liquid sample contained therein when the pipette is mounted in the mounting mechanism 28. Depending upon how the temperature control device 50 is mounted in pipette mounting mechanism 28, the pipette mounting mechanism may also be heated or cooled to the set temperature. Some time may be required for the sample in the pipette to reach the set temperature. Similarly, a temperature control device 52 may be placed in or in contact with the viscosity sensor 15 so as to heat or cool and maintain the temperature of the material forming flow channel 31 of the viscosity sensor 15 at the set temperature. This will tend to maintain the material flowing through the flow channel 31 at substantially the set temperature. As indicated, the temperature control devices may be peltier devices or other known temperature control devices. Further, temperature sensors can be positioned to measure the temperature of the sample liquid at various locations in the viscometer. For example, a temperature sensor can be included at one or more locations in the sensor membrane 37 along the flow channel 31 as shown in my prior referenced patents. Rather than separately controlling the temperature of separate components of the viscometer 22 as described above, the viscometer 22, or the parts thereof to be temperature controlled, may be mounted in a housing where the temperature within the housing, and thus the temperature of the entire viscometer or the parts thereof in the housing, are together temperature controlled.

As indicated in my prior referenced patents, the flow-through viscosity sensor described is very small, generally constructed of semiconductor materials or other materials used in microfabrication processes. For example, the pressure sensor membrane may be a portion of a silicon wafer, while the pressure sensor substrate and the channel substrate may be portions of a borosilicate glass wafer. The flow channel typically can be as small as about ten micrometers in width and about one micrometer in depth, with a length as short as about one hundred micrometers. Thus, the flow-through viscosity sensor is very small and small sample sizes can be used in determining viscosity. This small size of the flow-through viscosity sensor and the small amount of sample needed for viscosity testing means that the other viscometer components, such as the pipettes and the pump can also be made relatively small so the viscometer can easily be made as a relatively small portable unit.

Rather than making a portable viscometer, the same viscometer construction can be used to provide a stationary viscometer where samples of liquid to be tested can be collected from different locations in different pipettes and then transported to the viscometer and tested at the location of the viscometer.

If desired, a database of published or otherwise known viscosity values for liquids frequently measured or that might be measured can be stored in a memory in the viscometer controller. With such a database available, a user can easily display a known viscosity value from the database for a selected liquid and compare it to the viscosity value measured for a sample liquid thought to be the known liquid. Discrepancies between the published value and the measured value can indicate that the test liquid is not the liquid it is thought to be or can indicate problems with the viscometer so that the viscometer can be checked. In addition, for various reasons, it may be advantageous for a user from time to time to have access to the known viscosity values of particular liquids other than the liquid being tested at that time. Further, the viscometer may store a history of measured viscosity values with appropriate identification, again which may be used by the user of the viscometer for various purposes. For example, with such a history of measured viscosity values, a user can compare the viscosity of a liquid component being used in a manufacturing process at different times to ensure that the liquid component is within specifications required for the liquid component, or can determine and correlate a viscosity value of the component with particular desired attributes of the resulting product.

While the illustrated embodiment of the pump of the invention is shown and described as including a motor, lead screw, and push back to move the plunger in the pipette, various other means of moving the plunger in the pipette or of providing a precision discharge of sample liquid from a sample container can be used.

Whereas this invention is here illustrated and described with reference to embodiments thereof presently contemplated as the best mode of carrying out the invention in actual practice, it is to be realized that various changes may be made in adapting the invention to different embodiments without departing from the inventive concepts disclosed herein.

The invention claimed is:
1. A portable viscometer comprising:
  a viscosity sensor having a rectangular liquid flow channel with an interior space having four sides, wherein the interior space has a fixed depth, a liquid inlet connector coupled to the rectangular liquid flow channel, and at least two separate pressure sensors positioned along the rectangular liquid flow channel that measure a pressure drop of fully developed flow of a liquid flowing through the rectangular liquid flow channel based on an amount of deflection of at least a portion of a side wall of the rectangular liquid flow channel;

a dispensing pump mechanism adapted to couple with a positive displacement pipette that is adapted to contain a liquid, for which a measurement of viscosity is desired, so that operation of the dispensing pump mechanism, in cooperation with the positive displacement pipette, dispenses the liquid from the positive displacement pipette, and the viscosity sensor adapted to couple directly with the positive displacement pipette through the liquid inlet connector so that the liquid for which a measurement of viscosity is desired is forced into the viscosity sensor through the liquid inlet connector when dispensed from the positive displacement pipette; and a controller that controls operation of the viscometer and processes sensor data, the controller configured to control the viscosity sensor to measure, with the at least two separate pressure sensors, pressures of the liquid flowing through the rectangular liquid flow channel at an initially set flow rate, and automatically determine a flow rate of the liquid, that is distinct from the initially set flow rate, based on the pressures with the at least two separate pressure sensors, so that the liquid is subsequently injected into the rectangular liquid flow channel at the determined flow rate corresponding to subsequent pressures measured by the at least two separate pressure sensors, wherein the at least two separate pressure sensors include a first sensor and a second sensor that is separate from the first sensor, and the controller is further configured to determine whether the pressures measured with the at least two separate pressure sensors are less than threshold pressure for the viscosity measurement, including determining that at least one of the pressure measured with the first pressure sensor and the pressure measured with the second pressure sensor is less than the threshold pressure for the viscosity measurement and increase the flow rate of the liquid so that pressures, measured by the at least two separate pressure sensors, of the liquid flowing through the rectangular liquid flow channel at the increased flow rate are greater than the threshold pressure.

2. The portable viscometer according to claim 1, additionally including a display that shows test results.

3. The portable viscometer according to claim 1, wherein the controller includes a programmed microcontroller.

4. The portable viscometer according to claim 3, wherein the controller includes a user interface for inputting test variables.

5. The portable viscometer according to claim 1, wherein the positive displacement pipette includes a pipette barrel, and a pipette plunger sealingly and slidably positioned within the pipette barrel, wherein the pipette plunger includes a plunger end portion that extends from the pipette barrel by which the pipette plunger can be slidingly moved in the pipette barrel.

6. The portable viscometer according to claim 5, wherein the pipette plunger is slidingly movable in two opposite directions with respect to the pipette barrel, movement in a filling direction providing for filling of the pipette barrel with a liquid and movement in a dispensing direction providing for dispensing of liquid from the pipette barrel.

7. The portable viscometer according to claim 6, wherein the dispensing pump mechanism is adapted to move the pipette plunger in the dispensing direction with respect to the pipette barrel at a known rate to dispense the liquid in the pipette barrel from the pipette barrel at a known flow rate.

8. The portable viscometer according to claim 7, wherein the dispensing pump mechanism includes a motor, a lead screw coupled to the motor so that operation of the motor results in rotation of the lead screw, and a push back coupled to the lead screw so that rotation of the lead screw results in linear movement of the push back, said push back also coupled to the plunger end portion whereby linear movement of the push back moves the pipette plunger in the dispensing direction.

9. The portable viscometer according to claim 8, wherein the controller controls operation of the motor.

10. The portable viscometer according to claim 7, additionally including mounting mechanism for removably mounting the positive displacement pipette in the viscometer.

11. The portable viscometer according to claim 1, additionally including mounting mechanism for removably mounting the positive displacement pipette in the viscometer.

12. The portable viscometer according to claim 1, wherein the viscosity sensor comprises:

a monolithic sensor plate having (i) a smooth sensing surface corresponding to the side wall of the rectangular liquid flow channel and (ii) a plurality of separate pressure sensors at different locations; and a channel substrate with at least one flow channel formed therein having three side walls, a flow channel entrance, and a flow channel exit, wherein a combination of the channel substrate and the monolithic sensor plate collectively enables full containment of liquid during flow through the at least one flow channel, and the at least two separate pressure sensors of the plurality of separate pressure sensors in the monolithic sensor plate are positioned along the at least one flow channel sufficiently away from the flow channel entrance and flow channel exit so that a pressure drop of fully developed flow of the liquid in the at least one flow channel is measured as the liquid flows in the flow channel.

13. The portable viscometer according to claim 12, wherein the monolithic sensor plate includes a semiconductor material.

14. The portable viscometer according to claim 12, wherein the flow channel has a depth and the depth is greater than 1 micrometer and less than 1 mm.

15. The portable viscometer according to claim 1, wherein the portable viscometer stores a database of known viscosity values for a plurality of liquids.

16. The portable viscometer according to claim 1, wherein the viscometer stores a history of measured viscosity values.

17. The portable viscometer according to claim 1, wherein the controller includes communication means to enable communication between the controller and a remote computer.

18. The portable viscometer according to claim 1, additionally including at least one temperature control device to control the temperature of the liquid for which a measurement of viscosity is desired.

19. The portable viscometer according to claim 11, wherein the at least one temperature control device controls the temperature of the liquid for which a measurement of viscosity is desired in the positive displacement pipette prior to the liquid in the positive displacement pipette being forced into the viscosity sensor.

20. The portable viscometer according to claim 12, wherein the at least one temperature control device controls the temperature of the liquid for which a measurement of viscosity is desired as the liquid flows through the viscosity sensor.

21. The portable viscometer according to claim 1, wherein the at least two pressure sensors are positioned directly on a wall of the flow channel.

22. The portable viscometer according to claim 1, wherein the controller is configured to control the dispensing pump mechanism to dispense the liquid from the positive displacement pipette at the determined flow rate so that the liquid is injected into the rectangular liquid flow channel at the determined flow rate.

23. A portable viscometer comprising:
   a dispensing pump mechanism;
   a viscosity sensor having a rectangular liquid flow channel with an interior space having four sides, wherein the interior space has a fixed depth, a liquid inlet connector coupled to the rectangular liquid flow channel, and at least two separate pressure sensors positioned along the rectangular liquid flow channel that measure a pressure drop of fully developed flow of a liquid flowing through the rectangular liquid flow channel based on an amount of deflection of at least a portion of a side wall of the rectangular liquid flow channel;
   a mounting mechanism adapted to removably mount a positive displacement pipette adapted to contain a liquid for which a measurement of viscosity is desired, said mounting mechanism adapted to mount the positive displacement pipette in position to cooperate with the dispensing pump mechanism so that the positive displacement pipette couples directly with the viscosity sensor through the liquid inlet connector and operation of the dispensing pump mechanism dispenses the liquid from the positive displacement pipette, and to cooperate with the viscosity sensor so that the liquid for which a measurement of viscosity is desired is forced into the viscosity sensor through the liquid inlet connector when dispensed from the positive displacement pipette; and
   a controller that controls operation of the viscometer and processes sensor data, the controller configured to control the viscosity sensor to measure, with the at least two separate pressure sensors, pressures of the liquid flowing through the rectangular liquid flow channel at an initially set flow rate, and automatically determine a flow rate of the liquid, that is distinct from the initially set flow rate, based on the pressures with the at least two separate pressure sensors, so that the liquid is subsequently injected into the rectangular liquid flow channel at the determined flow rate corresponding to subsequent pressures measured by the at least two separate pressure sensors, wherein the at least two separate pressure sensors include a first sensor and a second sensor that is separate from the first sensor, and the controller is further configured to determine whether the pressures measured with the at least two separate pressure sensors are less than threshold pressure for the viscosity measurement, including determining that at least one of the pressure measured with the first pressure sensor and the pressure measured with the second pressure sensor is less than the threshold pressure for the viscosity measurement and increase the flow rate of the liquid so that pressures, measured by the at least two separate pressure sensors, of the liquid flowing through the rectangular liquid flow channel at the increased flow rate are greater than the threshold pressure.

24. The portable viscometer according to claim 23, additionally including at least one temperature control device to control the temperature of the liquid for which a measurement of viscosity is desired.

25. The portable viscometer according to claim 24, wherein the at least one temperature control device cooperates with the mounting mechanism to control the temperature of the liquid for which a measurement of viscosity is desired in the positive displacement pipette when the positive displacement pipette is mounted in the mounting mechanism prior to the liquid being forced from the positive displacement pipette into the viscosity sensor.

26. The portable viscometer according to claim 24, wherein the at least one temperature control device controls the temperature of the liquid for which a measurement of viscosity is desired as the liquid flows through the viscosity sensor.

27. The portable viscometer according to claim 23, wherein the dispensing pump mechanism includes a motor, a lead screw coupled to the motor so that operation of the motor results in rotation of the lead screw, and a push back coupled to the lead screw so that rotation of the lead screw results in linear movement of the push back, said push back adapted to mate with an end of a plunger extending from the positive displacement pipette when mounted in the mounting mechanism whereby linear movement of the push back moves the pipette plunger in a dispensing direction at a known rate to dispense the liquid from the positive displacement pipette at a known flow rate into the viscosity sensor.

28. A method of obtaining a measurement of viscosity of a liquid for which a measurement of viscosity is desired, comprising the steps of:
   obtaining a portable viscometer comprising:
      a dispensing pump mechanism;
      a viscosity sensor having a rectangular liquid flow channel with an interior space having four sides, wherein the interior space has a fixed depth, a liquid inlet connector coupled to the rectangular liquid flow channel, and at least two separate pressure sensors positioned along the rectangular liquid flow channel that measure a pressure drop of fully developed flow of a liquid flowing through the rectangular liquid flow channel based on an amount of deflection of at least a portion of a side wall of the rectangular liquid flow channel;
      a mounting mechanism adapted to removably mount a positive displacement pipette adapted to contain a sample liquid for which a measurement of viscosity is desired, said mounting mechanism adapted to mount the positive displacement pipette in position to cooperate with the dispensing pump mechanism so that the positive displacement pipette couples directly with the viscosity sensor through the liquid inlet connector and operation of the dispensing pump mechanism dispenses the sample liquid from the positive displacement pipette, and to cooperate with the viscosity sensor so that the sample liquid for which a measurement of viscosity is desired is forced into the viscosity sensor through the liquid inlet connector when dispensed from the positive displacement pipette; and a controller that controls operation of the viscometer and processes sensor data, the controller configured to control the viscosity sensor to measure, with the at least two separate pressure sensors, pressures of the liquid flowing through the rectangular liquid flow channel at an initially set flow rate, and automatically determine a flow rate of the liquid, that is distinct from the initially set flow rate, based on the pressures with the at least two separate pressure sensors, so that the liquid is subsequently injected into the rectangular liquid flow channel at the determined flow rate corresponding to subsequent pressures measured by the at least two separate pressure sensors;

obtaining a positive displacement pipette containing a liquid for which a measurement of viscosity is desired;

placing the positive displacement pipette containing the liquid for which a measurement of viscosity is desired in the mounting mechanism; and operating the portable viscometer to obtain a measurement of the viscosity of the liquid, for which a measurement of viscosity is desired, contained in the positive displacement pipette while the liquid flows through the portable viscometer, wherein the at least two separate pressure sensors include a first sensor and a second sensor that is separate from the first sensor, and the controller is further configured to determine whether the pressures measured with the at least two separate pressure sensors are less than threshold pressure for the viscosity measurement, including determining that at least one of the pressure measured with the first pressure sensor and the pressure measured with the second pressure sensor is less than the threshold pressure for the viscosity measurement and increase the flow rate of the liquid so that pressures, measured by the at least two separate pressure sensors, of the liquid flowing through the rectangular liquid flow channel at the increased flow rate are greater than the threshold pressure.

* * * * *

UNITED STATES PATENT AND TRADEMARK OFFICE
CERTIFICATE OF CORRECTION

PATENT NO. : 10,451,532 B2  
APPLICATION NO. : 13/094710  
DATED : October 22, 2019  
INVENTOR(S) : Baek Page 1 of 1

It is certified that error appears in the above-identified patent and that said Letters Patent is hereby corrected as shown below:

In the Claims

Claim 19, Column 10, Line 66, please delete "claim 11," and insert --claim 18,--;

Claim 20, Column 11, Line 5, please delete "claim 12," and insert --claim 19,--.

Signed and Sealed this
Fourteenth Day of January, 2020

Andrei Iancu
*Director of the United States Patent and Trademark Office*